US00PP08647P

United States Patent [19]

Meilland

[11] Patent Number: Plant 8,647

[45] Date of Patent: Mar. 22, 1994

[54] ROSE PLANT — MEIGORMON VARIETY

[75] Inventor: Alain A. Meilland, Antibes, France

[73] Assignee: The Conard-Pyle Company, West Grove, Pa.

[21] Appl. No.: 19,625

[22] Filed: Feb. 18, 1993

[51] Int. Cl.[5] ..... A01H 5/00

[52] U.S. Cl. ..... Plt./20

[58] Field of Search ..... Plt. 20, 21

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms attractive fully double blossoms which are red in coloration. The blossom coloration is Guardsman Red on the upper surface and Cardinal Red on the under surface. The bud shape is excellent. The blossoms are long lasting when cut and placed in a vase. The plant exhibits an upright growth habit, forms vigorous vegetation, and is well suited for cut flower production. A very good resistance to cryptogamic diseases is exhibited.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Meired variety (U.S. Plant Pat. No. 3,452). The Meired variety sometimes is known as the VISA variety in the United States. The male parent (i.e., the pollen parent) was the Meinastur variety (U.S. Plant Pat. No. 3,926). The Meinastur variety sometimes is known as the Alpha variety in the United States. The parentage of the new variety can be summarized as follows:

Meired × Meinastur.

The seeds resulting from the above pollination were sown and 14 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive fully double blossoms which are Guardsman Red on the upper surface and Cardinal Red on the under surface,
(b) forms buds which exhibit an excellent configuration,
(c) forms blossoms which exhibit an excellent life when cut and placed in a vase,
(d) exhibits vigorous vegetation,
(e) exhibits an upright growth habit,
(f) is particularly suited for cut flower production, and
(g) is not particularly affected by cryptogamic diseases.

The blossoms are particularly attractive at the bud stage.

The new variety well meets the needs of the horticultural industry and is well suited for use in the production of cut flowers under greenhouse conditions.

The new variety has been found to undergo asexual propagation in France by a number of routes, including budding, grafting, cuttage, etc. The characteristics of the new variety have been found to be strictly transmissible by such asexual propagation from one generation to another.

The new variety has been named the Meigormon variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during February while budded on *Rosa indica* understock and growing in greenhouses at Cap d'Antibes, France.

DETAILED DESCRIPTION

Figures 1, 2, 3, 4, 5, 6, 7, 8, 9, 10, 11, 12, 13, 14, 15, 16:
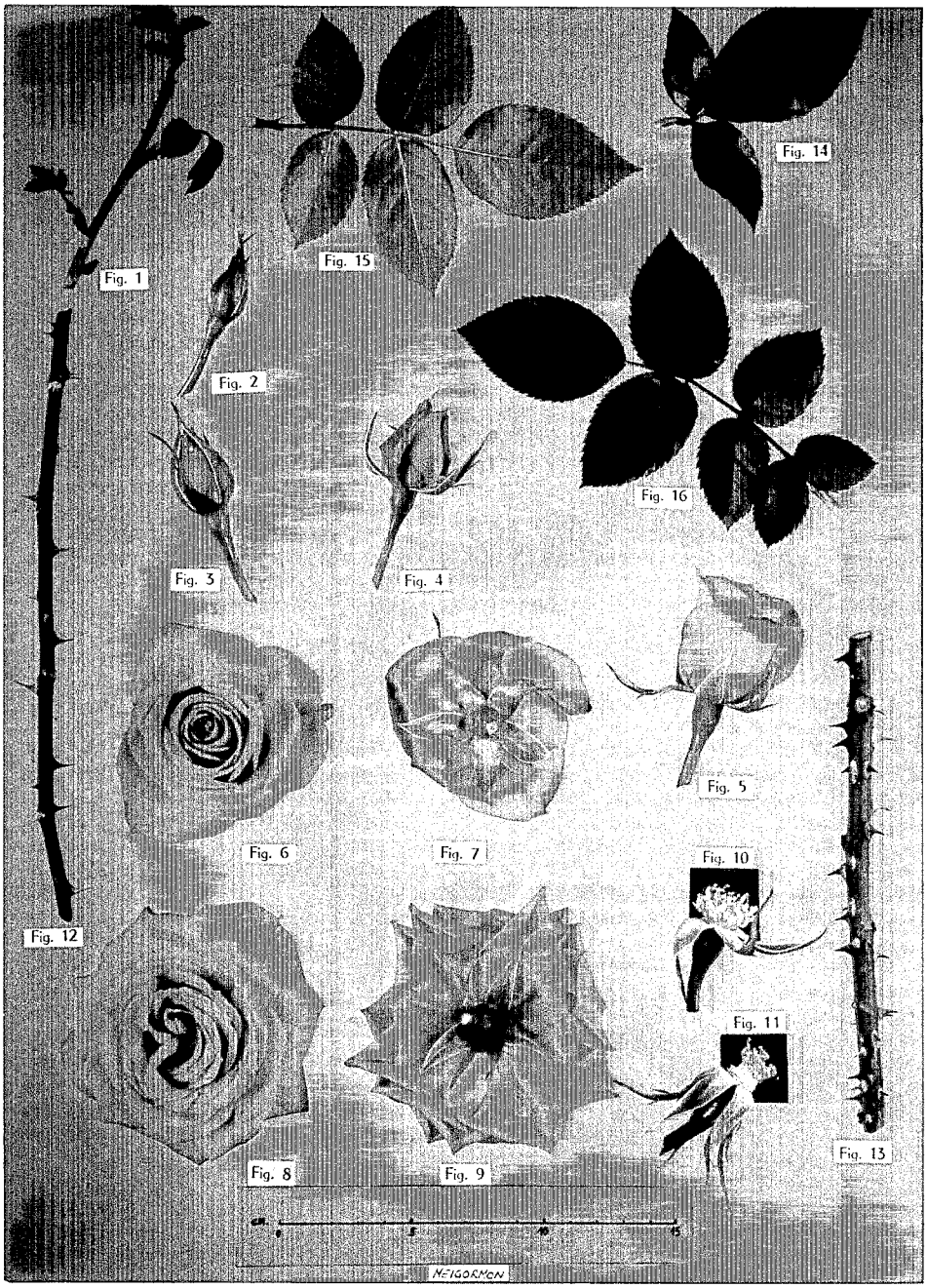
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptable showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets — plan view — upper surface.
FIG. 15 illustrates a specimen of a leaf with five leaflets — plan view — under surface.
FIG. 16 illustrates a specimen of a leaf with seven leaflets — plan view — upper surface.

The chart used in the identification of the colors is that of The Royal Horticultural Society (R.H.S. Colour Chart). The description is based on the observation of two year-old plants made during February while budded on *Rosa indica* understock and growing in greenhouses at Cap d'Antibes, France. The coloration in common terms precedes reference to the chart.

Class: Hybrid Tea.

Plant:

*Height.*—When plants are cut to a height of 85 cm., flowering stems are produced having a length of approximately 40 to 70 cm. When grown outdoors at Wasco, Calif., the plants commonly reach a height of approximately 110 cm. at the end of one growing season.

*Habit.*—Upright.

Branches:

*Color.*—Young stems: light green, Green Group 137C, and more or less stained with reddish coloration. Adult wood: dark green, Green Group 137A.

*Thorns.*—Size: medium. Quantity: average. Color: reddish on young stems and pinkish on mature wood.

Leaves:

Stipules.—Adnate, pectinate, fairly wide and linear.

*Petioles.*—Upper surface: striped reddish brown on young foliage and medium green on mature foliage with glandular edges. Under surface: light green, and bears very few prickles.

*Leaflets.*—Number: 3, 5, and 7 (most often). Shape: elliptic. Serration: single and regular. Texture: leathery. General appearance: dense, bright, full foliage. Color (young foliage): Upper surface: dark green, Green Group 137A stained with reddish coloration. Under surface: light grayish-green, Greyed-Green Group 191A stained with reddish coloration. Color (adult foliage): Upper surface: dark green, Green Group 137A. Under surface: medium green, Green Group 137B.

Inflorescence:

*Number of flowers.*—Usually one single bloom per stem.

*Peduncle.*—Smooth, medium green, more or less stained with reddish coloration, and sometimes slightly curved at the base of the receptacle. The length is approximately 7 to 8 cm. on average.

*Sepals.*—Upper surface: tomentose, greenish in coloration. Under surface: light green, more or less stained with reddish coloration, and the sepals have only slightly appendiculated edges.

*Buds.*—Shape: Egg-like. Length: approximately 3 cm. on average. Size: average. Color upon opening: Upper surface: dark Currant Red, Red Group 46A. Under surface: dark Cardinal Red, Red Group 53A.

Flower.—Shape: cup-like, and fully double. Diameter: approximately 9 to 11 cm. on average. Color (when opening begins): Upper surface: Guardsman Red, Red Group 45A, sometimes marbled and spotted with Greyed-Purple Group 187B. Under surface: Cardinal Red, Red Group 53A. Color (when blooming): Upper surface: Guardsman Red, Red Group 45A, sometimes marbled and spotted with Greyed-Purple Group 187B. Under Surface: Cardinal Red, Red Group 53A. Color (at end of opening): Upper surface: Guardsman Red, Red Group 45A, sometimes marbled and spotted with Greyed-Purple Group 187B. Under surface: Cardinal Red, Red Group 53A. Fragrance: none. Lasting quality: long lasting when cut and placed in a vase. Petal number: approximately 35 to 38 on average. Petal shape: oval to rounded. Texture: very consistent. Petal drop: good. Stamen number: approximately 190 on average. Anthers: pink-ochre at the center, with attachment to the filament being at a tip of the anther. Filaments: irregular in height, and dark fuschia in coloration. Pistils: approximately 143 on average. Stigmas: normal, straw-colored. Styles: dark fuschia in coloration, very tomentose near the base, and more or less twisted. Receptacle: medium green, more or less stained with reddish coloration, smooth, wide and in the shape of a funnel.

Development:

*Vegetation.*—Very vigorous.

*Blooming.*—Abundant and continuous when forced in a greenhouse. *Resistance to diseases.*—Very good. *Aptitude to be forced.*—Good

I claim:

1. A new and distinct variety of Hybrid Tea rose plant characterized by the following combination of characteristics:

(a) forms in abundance attractive fully double blossoms which are Guardsman Red on the upper surface and Cardinal Red on the under surface,
(b) forms buds which exhibit an excellent configuration,
(c) forms blossoms which exhibit an excellent life when cut and placed in a vase,
(d) exhibits vigorous vegetation,
(e) exhibits an upright growth habit,
(f) is particularly suited for cut flower production, and
(g) is not particularly affected by cryptogamic diseases;

substantially as herein shown and described.

* * * * * cm
0
5
10
15
NEIGORMON